United States Patent
Siciliano

(10) Patent No.: US 9,662,483 B2
(45) Date of Patent: May 30, 2017

(54) ROTARY TATTOO MACHINE

(71) Applicant: Gaston Siciliano, Doral, FL (US)

(72) Inventor: Gaston Siciliano, Doral, FL (US)

( * ) Notice: Subject to any disclaimer, the term of this patent is extended or adjusted under 35 U.S.C. 154(b) by 311 days.

(21) Appl. No.: 14/487,485

(22) Filed: Sep. 16, 2014

(65) Prior Publication Data
US 2016/0074645 A1 Mar. 17, 2016

(51) Int. Cl.
*A61M 37/00* (2006.01)

(52) U.S. Cl.
CPC .............................. *A61M 37/0076* (2013.01)

(58) Field of Classification Search
CPC .................. A61M 37/0076; A01K 11/005
See application file for complete search history.

(56) References Cited

U.S. PATENT DOCUMENTS

| | | | | |
|---|---|---|---|---|
| 4,204,438 A * | 5/1980 | Binaris | ............ | A61M 37/0076 30/362 |
| 5,279,552 A * | 1/1994 | Magnet | ............ | A61M 37/0076 604/47 |
| 5,551,319 A * | 9/1996 | Spaulding | ............ | A01K 11/005 30/362 |
| 7,207,242 B1 * | 4/2007 | Daigle | ............ | A61M 37/0076 30/362 |
| 9,393,395 B2 * | 7/2016 | Miller | ............... | A61M 37/0076 606/186 |
| 2012/0209307 A1 * | 8/2012 | Snijders | ............ | A61M 37/0076 606/186 |
| 2015/0202420 A1 * | 7/2015 | Miller | ............... | A61M 37/0076 606/186 |
| 2015/0352346 A1 * | 12/2015 | Webb | ............... | A61M 37/0076 606/185 |

* cited by examiner

*Primary Examiner* — David B Thomas
(74) *Attorney, Agent, or Firm* — Mark Terry

(57) ABSTRACT

A rotary tattoo machine is disclosed. The rotary tattoo machine comprises a machine body having a recess, a cam wheel for insertion into the recess of the machine body, comprising: a first retaining element; a cam located on top of, and coaxially with, the first retaining element, the cam coupled with the first retaining element, wherein the cam is configured for coupling with an axle of an electric motor, such that rotation of the axle rotates the cam, and wherein the cam includes a location on its top surface, such that the location is not coaxial with the cam; a needle driving shaft coupled with the location on the top surface of the cam, wherein the shaft extends upwards from the cam; and a drive element coupled to the shaft, wherein the drive element is further coupled with a needle.

16 Claims, 7 Drawing Sheets

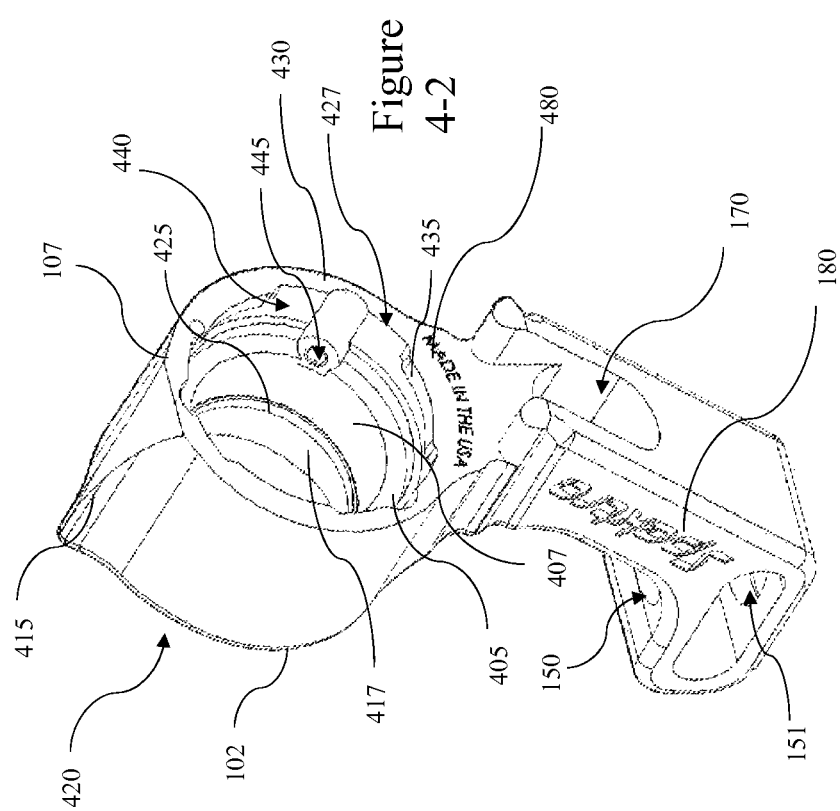

ROTARY TATTOO MACHINE

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The disclosed embodiments relate to the field of tattoo machines, and more specifically, the disclosed embodiments relate to the field of tattoo machines employing a cam wheel adapted to drive the linear motion of a tattoo needle.

BACKGROUND OF THE INVENTION

Conventional tattoo machines comprise a reciprocating needle that moves up and down, and in many cases, within a tubular or cylindrical structure that carries ink into the skin of an individual during the process of having a tattoo drawn on the individual's skin. The reciprocating needle typically punctures the skin at a high rate of frequency. Tattoo machine needles are installed in the machine and dipped in ink, which is sucked into the machine's tube system. Subsequently, the tattoo machine induces an up-and-down motion of the needle to puncture the top layer of the individual's skin and drive insoluble particles of ink into the dermal layer of skin.

Mechanically speaking, conventional tattoo machines comprise either a coil tattoo machine or a rotary tattoo machine. A coil tattoo machine employs an electromagnetic circuit to move the needle grouping up and down. Generally, a coil tattoo machine employs one or more DC coils and spring point(s) that induce the linear up and down motion of a bar that is coupled to the needle. Coil tattoo machines, however, are generally heavy and therefore difficult to maneuver during use. In addition, the electromagnetic switching of coil tattoo machines generates a significant amount of noise, which can turn off first-time customers who may already be hesitant about getting a tattoo.

Conventional rotary tattoo machines use an electric motor with a rotatable shaft having an offset cam at its apex, which offset cam is coupled perpendicularly with the needle to drive the needle in a reciprocating up and down motion. Rotary tattoo machines can offer several advantages to the coil machines in that a rotary tattoo machine is typically lighter in weight and substantially less noisy. Rotary tattoo machines, however, tend to exhibit problems with the longevity of the electric motor. Because the electric motor includes a rotatable shaft having an offset cam at its apex, the offset cam produces forces acting perpendicular to the longitudinal axis of the rotatable shaft. Such forces substantially perpendicular to, and acting on, the rotatable shaft translate to axial forces inside the motor causing damage to the motor's internal components resulting in the premature malfunctioning of the motor. This results in costly and time-consuming repairs and replacements, as well as annoyance to the user.

In view of the shortcomings of conventional rotary tattoo machines, there exists a need to overcome the problems with the prior art as discussed above, and particularly for a more efficient rotary tattoo machine that reduces or eliminates premature malfunctioning of the electric motor caused by the axial load forces on the motor shaft.

SUMMARY OF THE INVENTION

Briefly, according to an embodiment, a rotary tattoo machine is disclosed. The rotary tattoo machine comprises a machine body having a recess, a cam wheel for insertion into the recess of the machine body, comprising: a first retaining element; a cam located on top of, and coaxially with, the first retaining element, the cam coupled with the first retaining element, wherein the cam is configured for coupling with an axle of an electric motor, such that rotation of the axle rotates the cam, and wherein the cam includes a location on its top surface, such that the location is not coaxial with the cam; a needle driving shaft coupled with the location on the top surface of the cam, wherein the shaft extends upwards from the cam; and a drive element coupled to the shaft, wherein the drive element is further coupled with a needle.

The foregoing and other features and advantages of the embodiments will be apparent from the following more particular description of the preferred embodiments of the invention, as illustrated in the accompanying drawings.

BRIEF DESCRIPTION OF THE DRAWINGS

The subject matter, which is regarded as the invention, is particularly pointed out and distinctly claimed in the claims at the conclusion of the specification. The foregoing and other features and also the advantages of the invention will be apparent from the following detailed description taken in conjunction with the accompanying drawings.

FIG. 4-1 is an illustration of a cross sectional perspective view of one embodiment of the machine body of the rotary tattoo machine.

FIG. 4-2 is an illustration of a perspective view of one embodiment of the machine body of the rotary tattoo machine.

DETAILED DESCRIPTION

Figure 1:
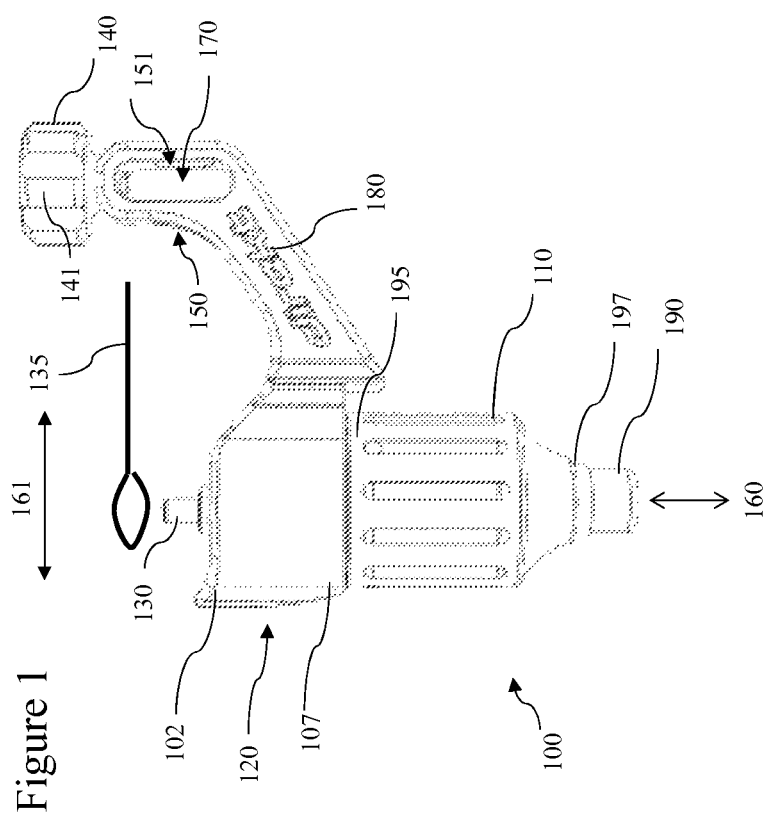
FIG. 1 is an illustration of a side view of the elements comprising a rotary tattoo machine, in accordance with one embodiment.

It should be understood that these embodiments are only examples of many adventitious uses of the innovative teachings herein. In general, statements made in the specification of the present application to not necessarily limit any of the various claimed inventions. Moreover, some statements may apply to some inventive features but not to others. In general, unless otherwise indicated, singular elements may be in the plural and vice versa with no loss of generality. In the drawings, like numerals refer to like parts through several views.

Applicant's rotary tattoo machine solves problems with the prior art by providing a simple and easy-to-use rotary tattoo machine that reduces or eliminates forces perpendicular to the axle of the rotary motor, thereby increasing the life-span of the rotary motor, which is a fundamental piece of a rotary tattoo machine. Further, the rotary tattoo machine provides a machine with a minimal number of component parts, thereby reducing the potential for failure or malfunction of the device. Also, the minimal number of component parts allows for quick and easy fabrication of the rotary tattoo machine. The rotary tattoo machine can be constructed of various metals, as well as non metallic materials.

The embodiments of the rotary tattoo machine will be described heretofore with reference to FIGS. 1 through 6 below. FIG. 1 is an illustration of a side view of the elements comprising a rotary tattoo machine 100, in accordance with one embodiment. The apparatus 100 may be composed of a conventional rotary tattoo machine material such as, aluminum, titanium, stainless steel and other metal alloys, or non-metallic materials, such as polymers, plastic, plastic derivatives, ceramic, carbon fiber, etc. One or more of the components that comprise the apparatus 100 may be milled from a single piece of metal or molded from a moldable material using conventional molding processes. The low number of parts, especially moving parts, and the simplicity of the design, results in a rotary tattoo machine 100 that is straightforward and easy to fabricate.

FIG. 1 shows a rotary tattoo machine 100 having an electric motor 525 (see FIG. 5) contained within an electric motor housing 110 coupled to a machine body 120. The rotary tattoo machine 100 further includes a drive element 135 (or drive bar) coupled to a shaft 130 of a cam wheel 200 (which will be more fully described in FIGS. 2-6 below). The drive element 135 may be coupled by using a fastener, such as a bolt, screw, snap, glue, mechanical element or the like deposited on the shaft 130, but this means of coupling the drive element to the cam wheel is not meant to be a limitation. The drive element is further mechanically coupled with a needle (not shown). The needle (not shown) may be deposited in a tube (not shown) and coupled to the machine body 120. The tube may be coupled with a grip (not shown) or be integral thereof. The drive element can, by way of example and not limitation, be formed from metal or metal alloy, a polymer, a ceramic any other suitable material, as well as any combination thereof.

The needle is positioned relative to the machine body 120 (along horizontal axis 161) such that it, or an element mechanically coupled with it, passes through a set of openings 150, 151 (better shown in FIGS. 4-2, 5 and 6) defined by the machine body and is substantially perpendicular or normal to the longitudinal axis of the motor shaft 310, which is represented by the longitudinal axial centerline 160. The shape of the machine body 120 can be similar to those used with conventional rotary tattoo machines.

FIG. 1 shows the machine body 120 has a first end 102 opposing a second end 107. The machine body 120 is a configuration that can be adapted to couple with various components. For example, the machine body 120 may also include a knob 140 to adjust the tube housing the needle (not shown in this illustration). The knob may include raised ridges 141 deposited along the surface of the knob 140 to assist the user to grip the knob. The machine body 120 may also be adapted to couple with other attachments such as a light or other attachment useful when tattoo artists perform their craft (not shown in this figure). In the present embodiment, the machine body 120 includes a logo 180. However, in other embodiments, the machine body 120 may also include graphics, pictures, or any in images that may be applied to the machine body 120. The graphics 180 may be embedded in the material comprising the machine body 120 or a graphics may be stamped, painted, stenciled, laser etched, printed, or engraved or so screened onto the machine body 120.

In the present embodiment, the machine body 120 has a plurality of voids 170 along the machine body 120. These voids 170 can be various shapes and sizes. The void 170 can be oval-shaped, but the shape is not meant to be limiting. An attachment (not shown) can be inserted into one or more of the voids 170.

Figure 3:
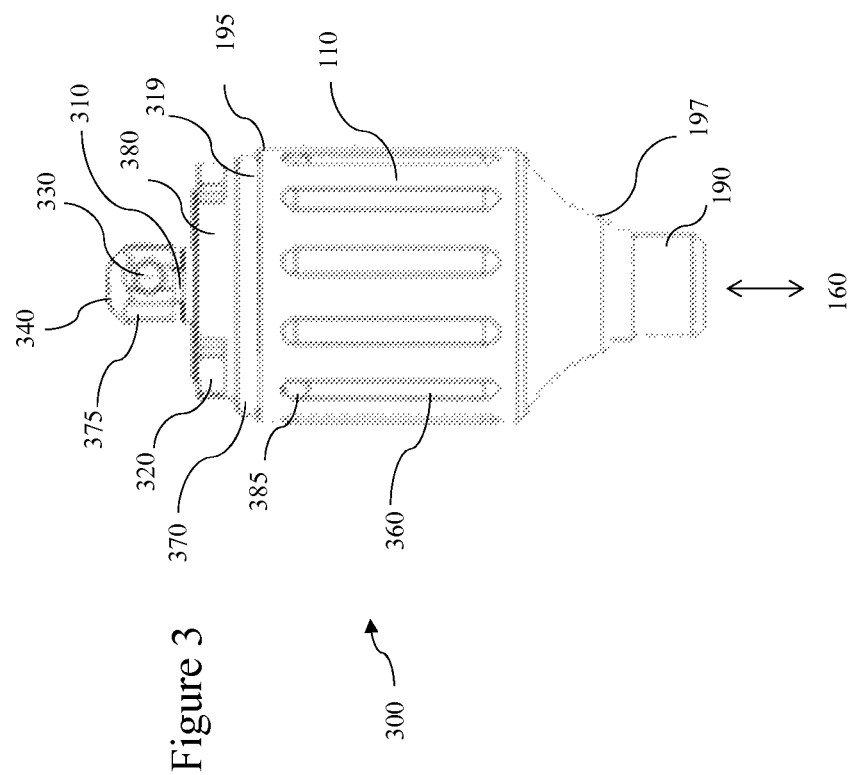
FIG. 3 is an illustration of a side view of electrical motor assembly of the rotary tattoo machine, in accordance with one embodiment.
Figure 5:
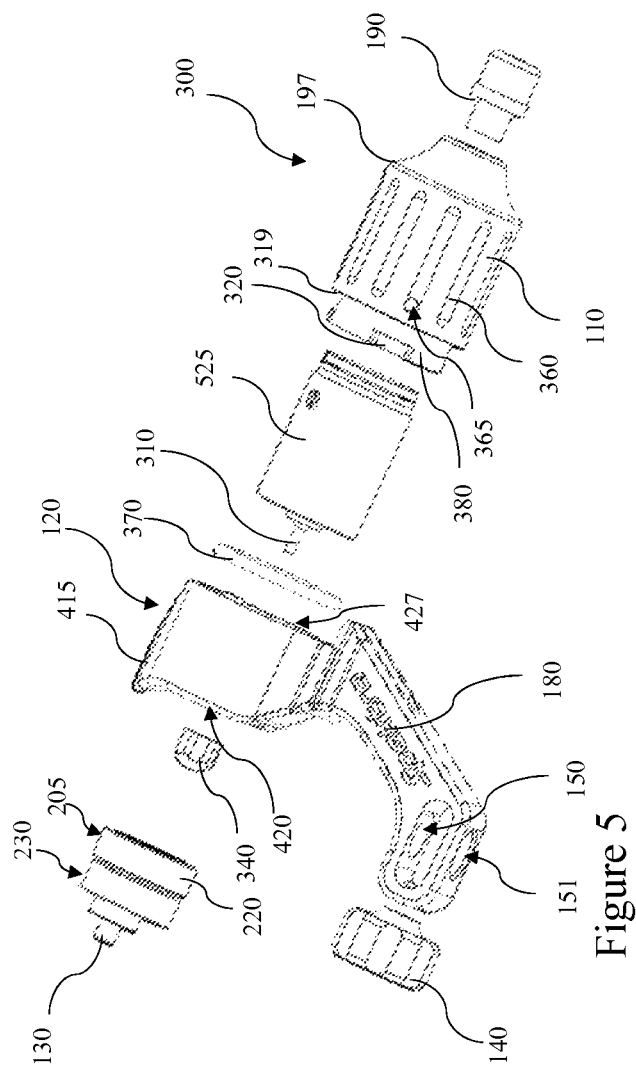
FIG. 5 is an illustration of a partially exploded side view of one embodiment of the rotary tattoo machine.

In the present embodiment, the electric rotary motor 525 is contained in a housing 110 having a tubular shaped body having a first end 195 opposing a second end 197 (and is more fully described in FIGS. 3 and 5). The motor is a conventional electrical motor, such as a conventional DC electric motor, and includes a rotatable shaft or axle 310 (illustrated in subsequent figures) extending from a portion thereof. The motor 525 can be energized using a conventional power source well known to those in the art. The power source is connected to the electric motor 525 at the power receiving part 190 (which may be an RCA connector, a jack, a clip cord, or the like) at the second end 197 of the motor housing 110. The second end 197 of the housing may define a shoulder having a cross section that is sloped or not perpendicular to the housing 120 of the machine body.

Figure 2:
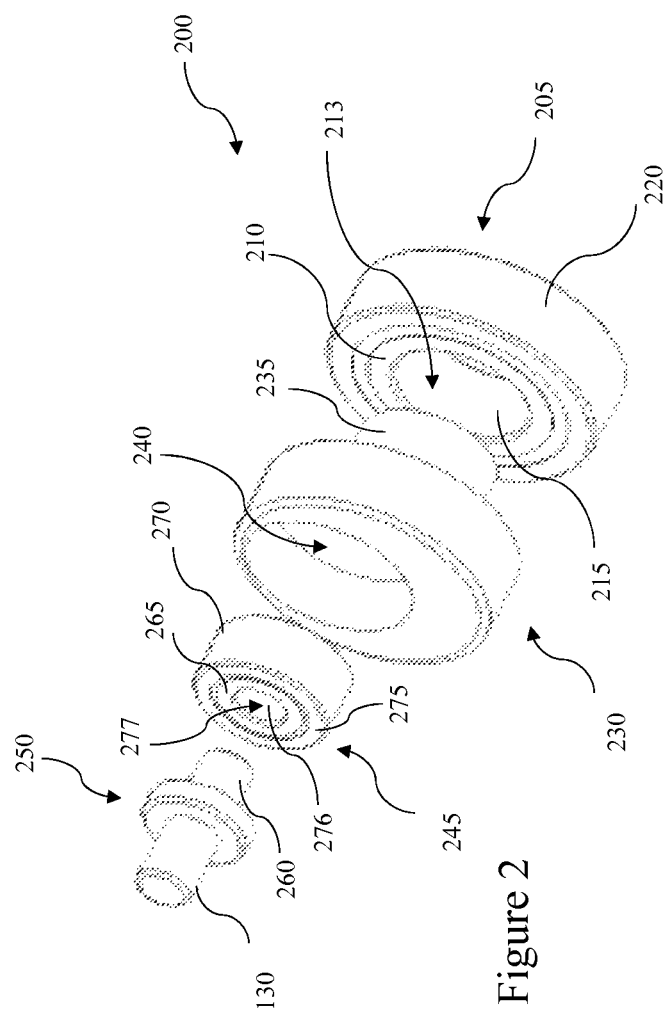
FIG. 2 is an illustration of exploded perspective view of one embodiment of the cam wheel of the rotary tattoo machine, in accordance with one embodiment.

FIG. 2 is an illustration of an exploded perspective view of the cam wheel 200. The cam wheel 200 is adapted for insertion into a recess or bore of the machine body 120. The cam wheel 200 includes a first bearing 205. The ball bearing used for the first bearing 205 is well known to those skilled in the art and is an element that constrains relative motion between moving parts to only a desired motion. The inner workings of the bearing 205 comprise a plurality of balls constrained by a retainer (not shown) that surrounds an inner race 210, which is co-centric with and surrounded by an outer race 220. The inner race 210 is coupled to the outer race 220 such that the inner race 210 can rotate freely within the outer race 220. The inner race 210 of the first bearing 205 may be adapted to directly or indirectly accept a gear of an electric motor axle of an electric motor 525 (shown in FIGS. 3 and 5), such that rotation of the electric motor axle rotates the inner race 210. The cylindrical shape of inner race 210 of the first bearing 205 defines a first bearing bore hole 213 and a first bearing bore hole wall 215.

The cam wheel 200 further includes a cylindrical cam 230 located on top of, and coaxially or concentrically with, the first bearing 205. The cylindrical cam 230 is coupled with the inner race 210 such that rotation of the inner race 210 rotates the cylindrical cam 230. In the present embodiment, the cylindrical cam 230 further includes a sleeve 235 having an inside and an outside that extends downward, and is adapted to fit into the bore hole 213 of the first bearing 205 and to be coupled to the first bearing bore wall 215. In one embodiment, the sleeve 235 is adapted to fit into the bore hole 213 and to be coupled to the first bearing bore wall 215 via a friction fit. A friction fit, or interference fit, is a fastening between two parts which is achieved by friction after the parts are pushed together, rather than by any other means of fastening. A friction fit is generally achieved by shaping the two mating parts so that one or the other, or both, slightly deviate in size from the nominal dimension. In a friction fit, one part slightly interferes with the space that the other occupies. The result is that both parts elastically deform slightly to fit together creating an extremely high force which results in extremely high friction between the parts. The friction fit between the sleeve 235 and the bore hole 213 may exhibit a strength index that allows conventional use of the machine 100 without the sleeve 235 detaching from the bore hole 213.

In another embodiment (not shown), the cylindrical cam 230 can be sized such that the entire cam fits into and is coupled to the bore hole wall 215 of the first bearing 205.

When the cylindrical sleeve 235 is coupled to the bore hole wall 215 of the first bearing 205, the cylindrical cam 230 can rotate while the outer race 220 of the first bearing 205 is restrained by the recess of the machine body 120 (described below). The cross-sectional outside diameter of the cam 230 is adapted to be slightly less than the cross-sectional outside diameter of the outer race 220 of the first bearing 205. The inside of the sleeve 235 may define a shape that is adapted to receive the gear 340 coupled to the shaft 310 of the electric motor 525 (see FIG. 3). In the present embodiment, the shape defined by the inside of the sleeve 235 of the cam is a six sided cylinder and corresponds to the hexagonal shape of the gear 340. Various shapes maybe used such that the inside of the sleeve 235 corresponds to, or matches, the shape of the gear 340.

The cam 230 also includes a recess or cylindrical shaped cutout 240 on its top surface for accepting a second bearing 245. The cutout 240 is eccentric or not coaxial with the cam 230. The cutout 240 is sized and adapted to receive the second bearing 245. In the present embodiment, the second bearing 245 is adapted for insertion into the cutout 240 and the bearing 245 may be coupled to the cutout 240 via friction fit. The bearing 245 includes an inner race 265, which is concentric with, and surrounded by, an outer race 270. The inner race 265 defines a bore hole 277 and a bore wall 276. When the bearing 245 is inserted into and coupled to the wall of the cutout 240 of the cam 230, the outer race 270 is rotatably attached to the cam 230. In one embodiment, in lieu of a cutout 240, other means of attaching the needle driving shaft 250 or second bearing 245 to cam 230 may be used, such as a protrusion or extending element on the top surface of the cam 230, or a mechanical element that mechanically connects the needle driving shaft 250 or second bearing 245 to cam 230. In another embodiment, needle driving shaft 250 and/or second bearing 245 are simply coupled to a location or area on the top surface of the cam 230.

In this document, the terms pivotally or rotatably attached, connected or coupled refers to a first element being attached to a second element in such a way that the first element and/or the second element may rotate or pivot in relation to the other element. Also, the term mechanically or indirectly connected or coupled refers to a first element being either directly or indirectly attached to a second element using mechanical means (i.e., intervening mechanical parts).

The cam wheel 200 further includes a needle driving shaft 250 that is located on top of and is coaxial with the second bearing 245. The needle driving shaft 250 is adapted for insertion into the borehole 277 of the second bearing 245. The needle driving shaft 250 is coupled with the inner race 265 of the second bearing 245 (such as via a friction fit) and includes a shaft 130 that extends upwards from the second bearing 245. In the present embodiment, the needle driving shaft 250 further comprises a shaft 260 extending downward and is adapted to fit into and is coupled to the second bearing bore wall 276 (such as via a friction fit). In one embodiment, shafts 130 and 260 comprise a singular shaft. In another embodiment, the shaft 130 has a smaller diameter than shaft 260, and a disc-shaped flange is located between the shafts 130 and 260, wherein said flange aids in coupling the needle driving shaft 250 to the drive element 135 (which is coupled to the needle).

The eccentric non-coaxial location of the second bearing 245 and the needle driving shaft 250 result in a back and forth linear motion of the needle driving shaft 250 represented by the line 161, which is perpendicular to longitudinal axial centerline 160, when the cam 230 is rotated by the motor shaft 310 of the electric motor 525 (via various intervening elements). This back and forth motion is what drives the needle mechanically coupled to the shaft 130 into the skin of the consumer.

The components of the cam wheel 200 can be fused or coupled by ultrasonic welding, arc welding, glue or the like, or by any combination thereof. The cam wheel 200 is sized so that it can be inserted into an opening in the first end 102 of the machine body 120, as is more fully described in FIGS. 5 and 6 below.

In one alternative embodiment, in lieu of bearing 205, a retaining element may be used. The purpose of bearing 205 is to retain the rotation of sleeve 235 such that it is constrained to rotation along axis 160 or closely thereof. This aids in the reduction of forces perpendicular (see forces 600 in FIG. 6) to axis 160, thereby increasing the life-span of the rotary motor 525. In this alternative embodiment, the retaining element may comprise a sleeve, a bushing, two magnetically opposed elements, etc.

FIG. 3 is a side view of one embodiment of electrical motor assembly 300. An electric motor housing 110 is adapted to contain an electric motor 525. The electric motor housing 110 comprises a cylindrical shaped body having a first end 195 opposing a second end 197. The electric motor can be inserted into the first end 195 of the electric motor housing 110 and fastened inside using a plurality of fasteners such as bolts or screws, or any combination thereof, that are adapted and sized to fit into holes 385 within the motor housing 110. In one alternative, screws and fasteners are not required, since a friction fit is used to couple the motor with the housing.

As mentioned above, the electric motor comprises a conventional electrical motor, such as a conventional DC electric motor, and includes a rotatable shaft 310 extending from a portion thereof. The motor 525 can be energized using a conventional power source well known to those in the art. The power source is connected to the electric motor at the power receiving part 190 at the second end of the electric motor.

In one embodiment, the first end 195 of the motor housing 110 further comprises a neck 380 having a tubular shape and is parallel and offset radially inward from the motor housing 110. The neck further defines a shoulder 319 (also illustrated in FIG. 5) providing a horizontal surface, and wherein an O-ring 370 rests on top of the shoulder 319. The length and outside diameter of the neck 380 is adapted and sized such that it allows the machine body 120 to receive the neck 380 of the machine housing 110 and is more fully described in FIGS. 4 and 5. The O-ring 370 is fabricated from material that is resilient in that it can compress and rebound to its original shape. The O-ring can be fabricated from a plastic like material or other materials well known to those skilled in the art.

A plurality of tabs 320 are deposited along the perimeter of the neck 380 of first end 195 of the motor housing 110.

The tabs 320 extend radially outward (in relation to the axial centerline 160) of the motor housing 110. The tabs 320 are sized and adapted to couple the motor to the machine body 120 and is more fully described in FIGS. 4-6. In the present embodiment, a set of three of tabs 320 is deposited along the perimeter or circumference of the neck 380. The tabs 320 are deposited on the edge of neck 380 proximal to the first end 195 of the motor housing 110. In one embodiment, the tabs 320 and elongated tabs 435 define a rectangular shape. The tabs 320 on the neck 380 correspond to the slots 440 along the rim 430 of the machine body 120 (more fully described in FIGS. 4 and 5). In other embodiments not shown, the tabs 320 may extend from the edge of neck 380 proximal to the first end 195 of the motor housing 110 and are adapted and sized such that the O-ring 370 rests on top of the shoulder 319 and below the tabs 320. The longitudinal length of the neck 380 is adapted or sized to comprise the O-ring 370 and the tabs 320 and such that the motor shaft 310 can be mechanically attached to the cam 230. In one embodiment, the tabs of neck 380 extend radially outward from the neck 380 of the housing by a dimension of approximately 1/32 to 1/8 inch. However, in other embodiments, this dimension can be varied depending on the size of the machine body, motor housing and the application for which the motor is being used and this size is not meant to be a limitation. Note also that although the embodiments disclose a removable electric motor, additional embodiments include a non-removable electric motor.

In yet another embodiment (not shown), the motor 525 or motor housing 110 may also be coupled to the machine body 120 by other means such as glue, welding, ultrasonic welding or fasteners, including but not limited to, screws or snaps or the like. The motor housing 110 also comprises elongated depressions 360 along or on the outside of the electric motor housing 110. In another embodiment (not shown), ridges deposited on the motor housing 110 may be used. These depressions 360 provide grip for a user to easily hold and rotate the motor housing 110. A gear 340 is coupled to the shaft using a fastener, such as a screw bolt 330. In another embodiment (not shown), the gear 340 may be integral with the shaft 310. The gear 340 may have teeth or protrusions 375 that define a shape that corresponds with the shape defined by the inside 235 of the sleeve of the cam 230. In another embodiment (not shown) the gear may be coupled directly to inner race 210 of the first bearing 205.

Figures 1, 4:
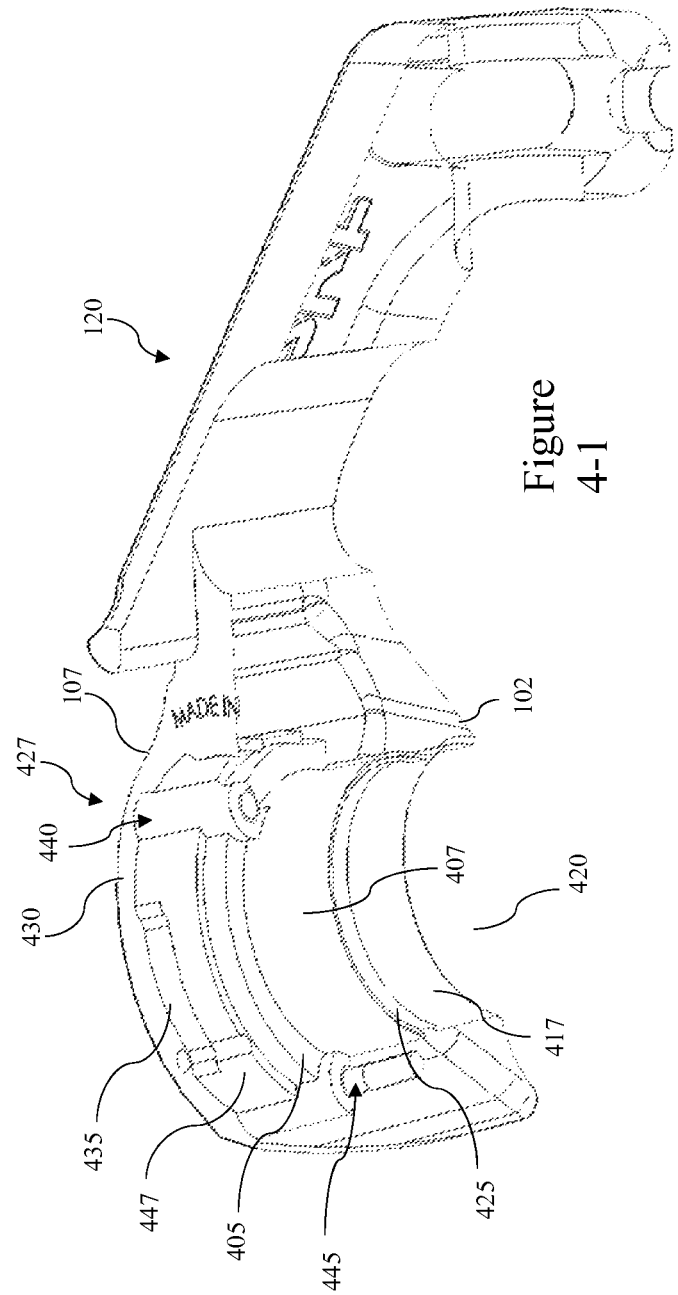

FIG. 4-1 is an illustration of a cross-sectional perspective view of machine body 120, and FIG. 4-2 is an illustration of a perspective view of the machine body 120, according to one embodiment. The recess of the machine body 120 (in to which the cam wheel 200 is inserted) has a tubular shape defining a wall. The recess comprises a first opening 427 at the end 107 of the machine body 120 and a second opening 420 at the end 102 of the machine body 120. The openings 420 and 427 are substantially circular in shape. The recess has three sections, a first section 447 adjacent to a second section 407 that is adjacent to a third section 417. The first section 447 has a wall defining a tubular shape that is coaxial with and proximate to the first opening 427. The second section 407 has a wall having a tubular shape that is adjacent, coaxial with, parallel to and offset radially inward from the wall of the first section 447, thereby defining a horizontal surface 405 or first shoulder. The first shoulder is substantially perpendicular and joined to the wall of first section 447. The third section 417 has a tubular shape and is adjacent, parallel to, coaxial with and offset radially inward from the wall of the second section 407, thereby defining a horizontal surface 425 or third shoulder. The third shoulder 425 is substantially perpendicular and joined to the wall of the second section 407. The surface or third shoulder 425 acts as a stop when the cam wheel 200 is received into the machine body 120 and prevents the cam wheel 200 from passing through the opening 420, thereby trapping the cam wheel 200 inside the wall of the section 407. The wall of the section 407 of the recess defines a cross-sectional internal diameter such that the cross-sectional outside diameter of the cam 230 can enter into the section 407 and pass through the opening 420. The outer diameter of first bearing 205 is sized slightly larger than the outside diameter of the cam 230 such that when the cam wheel 200 is inserted into the recess, the outer diameter of the outer race 220 of the first bearing 205 is greater than the cross sectional diameter of the 417 third section. Because of this, the shoulder 425 acts as a stop and prevents the first bearing 205 from exiting the second opening 420 (i.e., the bearing 205 rests on top of the shoulder 425). In another embodiment (not shown), a lip or ledge maybe used to reduce the internal diameter of the recess such that the outer race 220 of the first bearing 205 is prevented from exiting the second opening 420.

In the present embodiment, a plurality of holes 445 are provided along the shoulder 405 and adapted to receive a plurality of fasteners such that the fasteners retain the cam wheel 200 inside the section 407 of the recess when shoulder 425 traps and stops the cam wheel 200. In the present embodiment, the fasteners are screws (not shown) and the holes 445 along the cross section of the first shoulder are threaded to receive such screws.

In the present embodiment, the machine body 120 further defines a rim 430 surrounding the first opening 427. The electric motor 525 is contained within a housing 110 adapted to be inserted into the first opening 427 and to abut the rim 430 such that the electric motor axle 310 is rotatably attached to the cam 230. The rim 430 surrounding the first opening 427 of the recess comprises a plurality of elongated tabs 435 extending radially inward and spaced along the rim 430. The elongated tabs 435 decrease the internal diameter of the first opening 427 of the machine body 120. The spacing of the elongated tabs 435 along the rim 430 create a plurality of slots 440 along the rim where no elongated tabs 435 are deposited. In the present embodiment, three elongated tabs 435 are spaced such that three slots 440 are defined. However, in other embodiments (not shown), more tabs defining and more slots may be used. The slots 440 are sized so that the outward extending tabs 320 on the perimeter of the neck 380 of the motor housing 110 can enter into the slots 440 when the tabs 320 on the neck 380 are aligned with the slots 440. The tabs 320 on the neck 380 of housing 110 and the tabs 435 of the machine body 120 are sized such that the outward extending tabs 320 will prevent the motor housing 110 from entering or exiting into the machine body 120 if the tabs 320 on the neck 380 are aligned with the elongated tabs 435 in the rim 430. In one embodiment, each elongated tab 435 extends radially inward approximately 1/32 to 1/8 of an inch. However, in other embodiments, each elongated tab 435 can extend further or not as far into the first opening 427 depending on the dimension of the object being inserted into the machine body 102.

In one embodiment, the electric motor 525 can be coupled to the machine body 120 with a lock created by elongated tabs 435 on the rim 430 of the machine body 120, the tabs 320 on the neck 380, and the resilient force of the O-ring 370 located on the shoulder of the motor housing 110. To lock the motor 525 into the machine body 120, the first end 195 of the motor assembly 300 is received by or inserted to the machine body 120 such that the tabs 320 on the motor housing 110 extending radially outward are aligned and correspond to the corresponding slots 440 of the rim 430. A force acting towards and along the longitudinal axis of the machine body 120 then compresses the resilient O-ring 370 positioned on the shoulder of the motor housing 110 such that the tabs 320 on the motor housing pass by and clear the elongated tabs of the machine body 120. It should be noted that in the present embodiment, the neck 380 is further adapted such that the longitudinal length of the neck 380 is such that when the neck is received by the recess of the machine body 120, the O-ring 380 must be compressed for the tabs 320 on the motor housing to clear the elongated tabs 435 of the rim 430. After the tabs 320 of the motor clear the elongated tabs 435 of the machine body 120, a force normal to the longitudinal axial centerline 160 rotates the motor assembly 300 such that the tabs 320 on the motor housing 110 align with the elongated tabs 435. After the tabs 320 of the motor housing 110 and the elongated tabs 435 of the machine body 120 are aligned, the force along the centerline towards the machine body 120 compressing the resilient O-ring 370 is removed causing the O-ring 370 to bounce back to its original shape causing the tabs 320 on the electric motor housing 110 to engage the elongated tabs 435 of the machine body 120 thereby locking the motor assembly 300 into the machine body 120.

To unlock the motor 300 from the machine body 120, a force along the longitudinal centerline 160 towards the machine body 120 compresses the resilient O-ring 370 causing the tabs 320 on the motor housing 110 to disengage from the elongated tabs 435 of the machine body 120. A force perpendicular to the axial centerline 160 of the motor assembly 300 rotates the motor assembly 300 so that the tabs 320 of the motor assembly 300 align with the slots 440 of the rim 430. After the tabs 320 on the electric motor assembly 300 are aligned with the slots 440, the force acting toward the machine body 120 along the axial centerline 160 of the motor assembly 300 is removed allowing the motor assembly 300 to be removed from the machine body 120. In other embodiments (not shown), other means of coupling the motor to the machine body 120 are contemplated, including glue, arc welding, ultrasonic welding, fasteners, including but not limited to, screws, or snaps.

FIG. 4-1 also illustrates the set of openings 150, 151 on the machine body 120 through which the needle or needle grip element (not shown) can be positioned. As mentioned above, the needle when in place is perpendicular to the longitudinal axis of the electric motor shaft 310 (which is the same as axial centerline 160) and the axial longitudinal centerline of the needle driving shaft 250. The logo 180 is also shown on the drawing as well as information regarding where the machine body 120 was manufactured 480.

FIG. 5 is an illustration of a partially exploded side view of the rotary tattoo machine 100, in accordance with one embodiment. FIG. 5 also illustrates the cam wheel 200 when fully assembled. In one embodiment, the cam wheel 200 is fully assembled when: the sleeve 235 of the cam 230 is inserted into and coupled to the bore hole wall 215 of the inner race 210 of the first bearing 205; the second bearing 245 is received and coupled to the cylindrical cutout 240 of the cam 230; and the shaft 260 protruding downward from the needle driving shaft 250 is coupled to the inner race 265 of the second bearing 245.

In the present embodiment, the cam wheel 200 is sized such that the shaft 130 has clearance from the machine body 120 such that it can be mechanically coupled to a drive bar 135, needle or shaft when the cam wheel 200 is inserted into the end 107 of the machine body 120, trapped by the shoulder 425 and retained by the screws in the holes 445 of the shoulder 405. In the present embodiment, the outside of the sleeve 235 of the cam 230 is coupled to the bore hole wall 215 of the first bearing 205, and sleeve 235 is then coupled to the gear 340 and shaft 310 of the electric motor 525. As mentioned above, the gear 340 may be coupled to the shaft 310 or the gear 340 may be integral with the shaft 310. The electric motor assembly 300 is sized such that when the motor is coupled with the machine body 120, the motor shaft 310 and gear 340 couples with the sleeve 235.

Besides the cam wheel 200, the remainder of the rotary tattoo machine 100 is illustrated in an exploded view. The electric motor 525 is received by the motor housing 110 and secured by fasteners. In one embodiment, the electric motor 525 is secured into the motor housing 120 by screws (not shown) that received by threaded screw holes 385. In other embodiments, the electric motor 525 may be coupled to the machine housing 110 using a fastener such as a snap, bolt, glue, a friction fit or the like. FIG. 5 also provides a better illustration of the openings 150 and 151.

When the electric motor 525 is energized, the shaft 310 rotates. The motor can be energized by providing electrical current thereto and in a conventional manner, resulting in the rotation of the shaft 310. In one embodiment, a gear 340 maybe coupled to the shaft 310. The gear 340 may be secured to the shaft 310 with a set screw or plurality of set screws (not shown) in a hole along the gear. Other means of fastening the gear 340 to the motor shaft 310 are also contemplated and well known to those skilled in the art.

Figure 6:
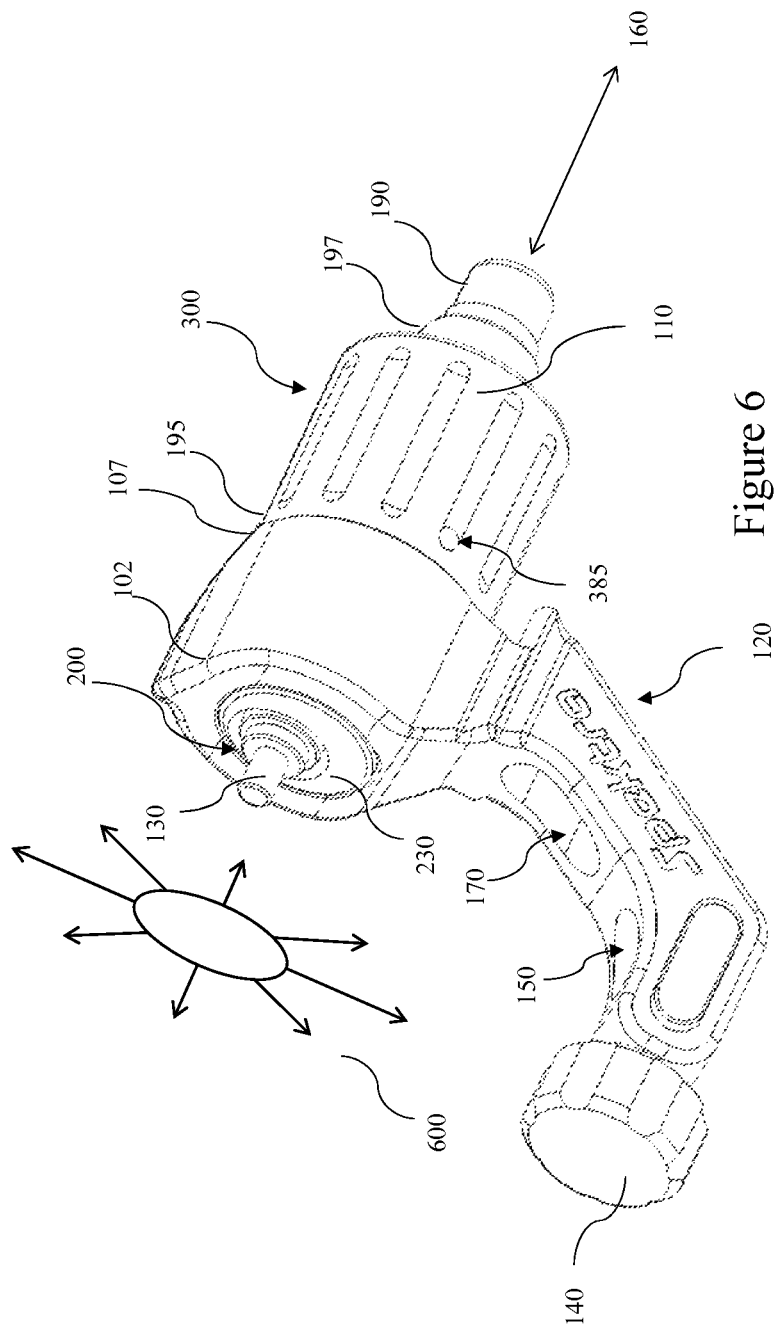
FIG. 6 is an illustration of a perspective view of an assembled embodiment of the rotary tattoo machine.

FIG. 6 is an illustration of a perspective view of one embodiment of the assembled rotary tattoo machine 100. The assembled cam wheel 200 is adapted for insertion into the recess of the machine body 120. As mentioned above, the outer diameter of the cam 230 is adapted to have a diameter slightly less than the outer diameter of the first bearing 205. The cross sectional diameter of the section 407 of the recess allows the cam 230 to enter the section 407. The shoulder 425 stops the outer race 220 of the first bearing 205 from entering into the third section 417 of the recess.

After the shoulder 425 stops the cam wheel 200 inside the recess, the cam wheel 200 is retained by a plurality of retaining screws (not shown), fasteners or the like inserted into threaded holes 445 along shoulder 405 that affix the outer race 220 of the first bearing 205 to the machine body 120. The inner race 210 of the first bearing 205 is not constrained and can rotate when the outer race 220 of the first bearing 205 is held in place within the recess of the machine body. In other embodiments, the cam wheel 200 may be affixed or coupled to the machine body 120 by arc welding, ultrasonic welding, glue or fasteners such that the fasteners do not prevent the inner race 210 of the first bearing 205 from rotating.

Once the cam wheel 200 is received into the recess of the machine body and stopped by the shoulder 425, the shaft 130 of the cam wheel 200 is such that it can be mechanically coupled with the drive bar 135 and/or the needle. The drive bar may further be mechanically coupled with a needle.

When the rotary tattoo machine 100 is fully assembled and the motor 525 is energized, the shaft 310 rotates. As the shaft 310 rotates, and the force generated by the rotating shaft 310 rotates the sleeve 235, the inner race 210 of the first bearing 205 also rotates. The needle driving shaft 250 is coupled to the inner race 265 of the second bearing 245 and the second bearing 245 is positioned inside of the eccentric or non-coaxial cutout 240 of the cam 230. The eccentric or non-coaxial location of the shaft 130 results in a back and forth motion of the drive bar and thus also the needle. The band and forth motion of the needle punctures the top layer of the skin and drives insoluble particles of ink into the dermal layer of skin. As cam 230 rotates, a force 600 (or set of forces) acts on shaft 130, bearing 245 and on cam 230 in directions perpendicular to the axial centerline 160 of the device. In one embodiment, forces 600 comprise all forces that radiate outwards perpendicularly from the longitudinal axis 160, which forces can be attributed to the centripetal forces experienced by needle driving shaft 250 as it travels along a circular path due to the non-concentric location of cutout 240 in the cam 230. These forces 600 are thus absorbed or captured by shaft 130 (and needle driving shaft 250, by extension), bearing 245 and cam 230. In the prior art, such forces would transfer to the rotatable shaft of the electric motor and translate to forces inside the motor causing damage to the motor resulting in the pre-mature malfunctioning of the motor. In the embodiments herein, shaft 130 (and needle driving shaft 250, by extension), bearing 245 and cam 230 absorb or substantially absorb the forces 600 perpendicular to and acting on the rotatable shaft 310. This translates into a decrease of forces that act upon the motor causing damage to the motor resulting in the pre-mature malfunctioning of the motor. The disclosed embodiments are not limited for use on tattoo machines and can be used in other rotary machines having a shaft coupled to a rotary shaft Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of Applicant's apparatus.

What is claimed is:

1. A rotary tattoo machine, comprising:
a machine body having a recess; and
a cam wheel for insertion into the recess of the machine body, comprising:
a first retaining element;
a cam located on top of, and coaxially with, the first retaining element, the cam coupled with the first retaining element, wherein the cam is configured for coupling with an axle of an electric motor, such that rotation of the axle rotates the cam, and wherein the cam includes a location on its top surface, such that the location is not coaxial with the cam;
a needle driving shaft coupled with the location on the top surface of the cam, wherein the shaft extends upwards from the cam;
a drive element coupled to the shaft, wherein the drive element is further coupled with a needle
wherein the recess in the machine body comprises a substantially cylindrical bore adapted to accept the first retaining element, and wherein the bore includes a shoulder that prevents the first retaining element from traveling through the bore; and
wherein the cam includes a sleeve adapted for insertion into, and coupling with, the first retaining element, such that rotation of the sleeve rotates the first retaining element and the cam.

2. The rotary tattoo machine of claim 1, wherein the sleeve of the cam is adapted for coupling with the axle of the electric motor, such that rotation of the axle rotates the cam.

3. The rotary tattoo machine of claim 2, wherein the sleeve that is inserted into, and coupled with, the first retaining element defines a six sided interior adapted to receive a hexagonal gear coupled to the axle of the electric motor.

4. The rotary tattoo machine of claim 3, wherein the location on the top surface of the cam comprises a cylindrical bore that is not coaxial with the cam.

5. A rotary tattoo machine, comprising:
a machine body having a recess; and
a cam wheel for insertion into the recess of the machine body, comprising:
a first bearing having an inner race;
a cam located on top of, and coaxially with, the first bearing, the cam coupled with the inner race of the first bearing, wherein the cam is configured for coupling with an axle of an electric motor, such that rotation of the axle rotates the cam, and wherein the cam includes a location on its top surface, such that the location is not coaxial with the cam;
a second bearing for coupling with the location on the top surface of the cam;
a needle driving shaft coupled with an inner race of the second bearing, wherein the shaft extends upwards from the second bearing; and
a drive element coupled to the shaft, wherein the drive element is further coupled with a needle.

6. The rotary tattoo machine of claim 5, wherein the recess in the machine body comprises a substantially cylindrical bore adapted to accept the first bearing, and wherein the bore includes a shoulder that prevents the first bearing from traveling through the bore.

7. The rotary tattoo machine of claim 6, wherein the cam includes a sleeve adapted for insertion into, and coupling with, an inner race of the first bearing, such that rotation of the sleeve rotates the inner race of the first bearing and the cam.

8. The rotary tattoo machine of claim 7, wherein the sleeve of the cam is adapted for coupling with the axle of the electric motor, such that rotation of the axle rotates the cam.

9. The rotary tattoo machine of claim 8, wherein the sleeve that is inserted into, and coupled with, the inner race of the first bearing defines a six sided interior adapted to receive a hexagonal gear coupled to the axle of the electric motor.

10. The rotary tattoo machine of claim 9, wherein the location on the top surface of the cam comprises a cylindrical bore that is not coaxial with the cam, and wherein the cylindrical bore is adapted to accept the second bearing.

11. A rotary tattoo machine, comprising:
a machine body having a recess; and
a cam wheel for insertion into the recess of the machine body, comprising:
a first bearing having an inner race;
a cylindrical cam located on top of, and coaxially with, the first bearing, the cylindrical cam including a tubular element that resides within the inner race of the first bearing, wherein the tubular element is configured for coupling with an axle of an electric motor such that rotation of the axle rotates the cylindrical cam and wherein the cylindrical cam includes a location on its top surface, such that the location is not coaxial with the cylindrical cam;
a second bearing for coupling with the location on the top surface of the cylindrical cam;
a needle driving shaft coupled with an inner race of the second bearing, wherein the shaft extends upwards from the second bearing; and a drive element coupled to the shaft, wherein the drive element is further coupled with a needle.

12. The rotary tattoo machine of claim 11, wherein the recess in the machine body comprises a substantially cylindrical bore adapted to accept the first bearing, and wherein the bore includes a shoulder that prevents the first bearing from traveling through the bore.

13. The rotary tattoo machine of claim 12, wherein the cam includes a sleeve adapted for insertion into, and coupling with, an inner race of the first bearing, such that rotation of the sleeve rotates the inner race of the first bearing and the cam.

14. The rotary tattoo machine of claim 13, wherein the sleeve of the cam is adapted for coupling with the axle of the electric motor, such that rotation of the axle rotates the cam.

15. The rotary tattoo machine of claim 14, wherein the sleeve that is inserted into, and coupled with, the inner race of the first bearing defines a six sided interior adapted to receive a hexagonal gear coupled to the axle of the electric motor.

16. The rotary tattoo machine of claim 15, wherein the location on the top surface of the cam comprises a cylindrical bore that is not coaxial with the cam, and wherein the cylindrical bore is adapted to accept the second bearing.

\* \* \* \* \*